(12) United States Patent
Carson et al.

(10) Patent No.: US 8,354,478 B2
(45) Date of Patent: Jan. 15, 2013

(54) SILICONE POLYURETHANE BLENDS

(75) Inventors: John C. Carson, Union City, NJ (US); Albert A. Zofchak, Holmdel, NJ (US)

(73) Assignee: Alzo International, Inc., Sayreville, NJ (US)

( * ) Notice: Subject to any disclaimer, the term of this patent is extended or adjusted under 35 U.S.C. 154(b) by 618 days.

(21) Appl. No.: 12/283,475

(22) Filed: Sep. 12, 2008

(65) Prior Publication Data
US 2009/0232752 A1 Sep. 17, 2009

Related U.S. Application Data

(60) Provisional application No. 60/993,445, filed on Sep. 12, 2007.

(51) Int. Cl.
*C08F 20/00* (2006.01)
*A61K 8/00* (2006.01)

(52) U.S. Cl. ............... 525/446; 8/405; 424/59; 424/65; 424/70.12; 424/76.1; 512/2; 514/772.3; 525/453

(58) Field of Classification Search ............... 525/446, 525/453; 512/2; 8/405; 424/59, 65, 70.12, 424/76.1; 514/772.3
See application file for complete search history.

(56) References Cited

U.S. PATENT DOCUMENTS

| 5,017,322 | A | * | 5/1991 | Brooks | 264/255 |
| 5,538,793 | A | * | 7/1996 | Inokuchi et al. | 428/407 |
| 5,707,612 | A | * | 1/1998 | Zofchak et al. | 424/69 |
| 6,262,170 | B1 | * | 7/2001 | Kilgour et al. | 524/731 |
| 6,315,991 | B1 | * | 11/2001 | Zofchak et al. | 424/70.28 |
| 6,936,686 | B2 | | 8/2005 | Awad | |
| 2002/0155962 | A1 | * | 10/2002 | Cincotta et al. | 510/119 |
| 2003/0068348 | A1 | * | 4/2003 | Ferrari et al. | 424/401 |
| 2003/0109623 | A1 | * | 6/2003 | Gornowicz et al. | 524/492 |
| 2004/0037796 | A1 | | 2/2004 | Cottard et al. | |
| 2005/0100568 | A1 | | 5/2005 | De Mul et al. | |
| 2005/0276776 | A1 | * | 12/2005 | Liechty et al. | 424/70.12 |
| 2005/0287099 | A1 | | 12/2005 | Liechty et al. | |
| 2006/0210508 | A1 | * | 9/2006 | Gamez-Garcia | 424/70.11 |
| 2006/0293431 | A1 | | 12/2006 | Kani et al. | |
| 2007/0048240 | A1 | | 3/2007 | Slavashevich et al. | |
| 2009/0185984 | A1 | * | 7/2009 | Gutkowski et al. | 424/49 |

FOREIGN PATENT DOCUMENTS

| FR | 2870114 A1 | 11/2005 |
| JP | 2006342165 A | 12/2006 |

OTHER PUBLICATIONS

Notification of Transmittal of the International Search Report and the Written Opinion of the International Searching Authority, or the Declaration.

* cited by examiner

*Primary Examiner* — Ling Choi
*Assistant Examiner* — Chun-Cheng Wang
(74) *Attorney, Agent, or Firm* — Henry D. Coleman; R. Neil Sudol; William J. Sapone (57) ABSTRACT

The invention describes the unexpected characteristics of blends, including crosslinked reaction products of elastomeric silicone polymers with various polyurethanes and their applications in personal care products.

4 Claims, 9 Drawing Sheets

FIGURE 2
POLYDERM PPI-DGDIS
INCI NAME: POLYGLYCEROL-2 DIISOSTEARATE / IPDI COPOLYMER CAS# 214975-67-4

CHEMICAL CLASS: Hydroxy Ester Polyurethane
Appearance: Clear Straw Colored Viscous Liquid
Solubility: Oil Soluble
Ionic Nature: Nonionic Function: Make-up: Substantive Pigment Dispersant-Suspending Agent-Binder
Lipstick: Gloss-Shine-Transfer Resistance-Moisturizer
Skin: Film Former-Emolliency-Conditioning-Water Resistance

FIGURE 3

POLYDERM PPI - G7-CA

INCI NAME: GLYCERETH-7 / POLYGLYCERYL-2 / PEG-15 COCAMINE / IPDI COPOLYMER (PROPOSED)

Cas # 373387-50-9

FIGURE 4
POLYDERM PPI-GRC
GLYCEROL DIRICINOLEATE / IPDI COPOLYMER CAS# 351424-97-0

$R_{10}$ (Radical) = $CH_2 - CH = CH - (CH_2)_7$

CHEMICAL CLASS: Hydroxy Ester Polyurethane
Appearance: Clear Amber Viscous Liquid
Solubility: Oil Soluble
Ionic Nature: Nonionic Function: Make-up: Substantive Color Dispersant-Binder
Lipstick: Glass-Shine-Transfer Resistance-Moisturizer
Skin: Film Former-Emolliency-Conditioning FIGURE 5
POLYDERM PPI-PGR
PROPYLENE GLYCOL DIRICINOLEATE / IPDI COPOLYMER CAS# 351425-00-8

$R_{10}$ (Radical) = $CH_2 - CH = CH - (CH_2)_7$

CHEMICAL CLASS: Hydroxy Ester Polyurethane
Appearance: Clear Amber Viscous Liquid
Solubility: Oil Soluble
Ionic Nature: Nonionic Function: Make-up: Substantive Color Dispersant-Binder
Lipstick: Glass-Shine-Transfer Resistance-Moisturizer
Skin: Film Former-Emolliency-Conditioning FIGURE 6
POLYDERM PPI-SA-15
INCI NAME (Proposed): PEG-15 SOYAMINE / IPDI COPOLYMER

$X+Y = 15$ Ave.

$R_{18}$ = Soya Radical

CHEMICAL CLASS: Polyamine
Appearance: Clear Amber Viscous Liquid
Solubility: Water Soluble
Ionic Nature: Cationic Function: Skin & Hair Conditioner

FIGURE 7
POLYDERM PPI-SA
INCI NAME: DI - PEG-2 SOYAMINE / IPDI COPOLYMER CAS# 239802-47-2

$X = 1$
$R_{18}$ = Soya Radical

CHEMICAL CLASS: Polyurethane - Polyamine
Appearance: Clear Amber Viscous Liquid
Solubility: Oil Soluble
Ionic Nature: Cationic Function: Skin & Hair Conditioner

FIGURE 8A

POLYDERM PPI-SI-L
INCI NAME (Proposed): BIS PEG-1 DIMETHICONE / IPDI COPOLYMER SILOXANES & SILICONES, DI – Me,3 – HYDROXYPROPYL GROUP TERMINATED,ETHOXYLATED   CAS # 102783-01-7

3 – ISOCYANITOMETHYL – 3,5,5-TRIMETHYLCYLOHEXYL ISOCYANATE
CAS # 4098-71-9

FIGURE 8B

SILOXANES, SILICONES, DI – Me,3 – HYDROXYPROPYL GROUP – TERMINATED,ETHOXYLATED / IPDI COPOLYMER

SILICONE POLYURETHANE BLENDS

RELATED APPLICATIONS

This application claims the benefit of priority of provisional application Ser. No. U.S. 60/993,445, of identical title, filed Sep. 12, 2007, the entire contents of which application are incorporated by reference in their entirety herein.

FIELD OF THE INVENTION

The present invention relates to blends of silicone polymers (in particular, silicone elastomers) and polyurethanes (both diurethanes and polyurethanes) which may be used in personal care products. The silicone polymers and polyurethanes may be blended or reacted to produce crosslinked compositions. The constituents are combined in a manner which produces superior characteristics related to the mixture including enhanced emolliency with greater skin compatibility and wetting. These compositions are found to be particularly useful for including in personal care products, and in particular, hair care products and skin products where emolliency, wetting, storage stability and/or film-forming properties are important.

BACKGROUND OF THE INVENTION

Silicone polymers are well known materials in the cosmetic and personal care industries. These materials are composed of repeating dimethylsiloxanes units which may be terminated in various ways. These terminations, in large measure, determine their properties (i.e. hydrophilicity) and their ability to react with other materials. In addition to the terminal groups, the polydimethylsiloxanes themselves can have widely varying molecular weights and may be linear, branched or crosslinked in structure. Each of these variations will produce widely varying properties and uses. Some of the silicone polymers that are more useful in cosmetic and personal care products are the silicone elastomers. These are highly cross-linked silicone polymers that have physical properties that resemble those of rubber—in that they deform and stretch when force is applied, they bounce when dropped to the floor and they exhibit an elastic memory, i.e. exerting a force to return to their original shape once they are deformed. When diluted (or dispersed) in a solvent (or liquid) these elastomers find use as film forming materials. Further, when used in cosmetics or personal care products, the elastomer solutions or dispersions produce a very smooth, non-oily, dry feeling lubricity on skin and hair. This effect is especially appreciated in make-up products that contain pigments and because the product application is greatly improved and because the elastomer film can reduce the rubbing off of the pigments once the product is applied and has dried. The silicone elastomers of particular interest are those described in U.S. Pat. No. 6,936,686 which is directed to the preparation and use of silicone elastomers that are crosslinked as a solution in either a low viscosity silicone oil, a hydrocarbon oil, a cyclomethicone or mixtures thereof.

Other polymers in addition to silicone elastomers are used in personal care and cosmetic products. Materials such as polyethylenes, polybutenes and polydecenes are used as emollients and vehicles in a variety of products. Vinyl polymers with pendant ester or acid groups are used as thickeners in aqueous systems and as film formers and hair fixatives. Polyurethanes of several different types are used as hair fixatives, film forming agents, viscosity modifiers and hair and skin conditioners. In general, these polyurethanes have a noticeable tacky feel. It is thought that this tackiness contributes to the outstanding deposition and film forming properties of the polyurethanes and, while this may be desirable in some applications, it often interferes with a feeling of lubricity which is usually desirable in personal care products. It is with these properties in mind that we sought to combine the silicone elastomers with the polyurethanes in order to combine their properties, hopefully to reduce the tackiness, to obtain new properties and to develop a wider range of applications for all of the polymers.

OBJECTS OF THE INVENTION

It is an object of this invention to produce blends of various polyurethane and diurethane compounds with silicone elastomers that have uses in cosmetic and personal care products. The property modifications that occur because of making the mixtures can be used to produce finished formulations that have expanded applications with improved performance.

It is an object of this invention to make mixtures of various polyurethane and diurethane compounds with silicone elastomers that have improved storage properties.

It is an object of this invention to make mixtures of various polyurethane and diurethane compounds with silicone elastomers that have improved compatibility with water and polar solvents thus giving them wider applications in products.

It is an object of this invention to make mixtures of various polyurethane and diurethane compounds with silicone elastomers in order to produce products that have changed (non-gelled) rheologies that provide improved handling and mixing properties that improve the process ability and storage stability of the silicone elastomer gels.

Any one or more of these and/or other objects of the invention may be readily gleaned from the description of the invention which follows.

BRIEF DESCRIPTION OF THE FIGURES

FIGS. 1-8 depict a number of commercially available polyurethane compositions (based upon carbon or silicone backbones) which may be used to produce silicone elastomer/polyurethane compositions according to the present invention. These compositions are available from Alzo International, Inc. of Sayreville, N.J. In FIGS. 1-8, n, if present, is an integer from 5 to 100.

In FIG. 2, n is 5 to 100.

In FIG. 8, x is 6-360 and y is 5-100.

BRIEF DESCRIPTION OF THE INVENTION

The present invention relates to a combination of a silicone elastomer and a polyurethane (including a diurethane) composition which produces a polymeric mixture which provides many of the favorable attributes of the silicone elastomer (as an emollient or water-repellent material with favorable film-forming characteristics). In the present invention, a silicone elastomer ranges from about 0.5% to about 99.5% by weight and a polyurethane (which term includes a diurethane compound) ranges from about 0.5% to about 99.5% by weight of a mixture of the silicone elastomer and the diurethane. In preferred embodiments, the silicone elastomer ranges from about 5% to about 95% by weight of the mixture and this composition/mixture, may be added to any number of personal care products in order to instill favorable property of the silicone elastomer and polyurethane compound.

The simplest illustration of the concept is to use a polyurethane prepared from castor oil by the addition of isophorone diisocyanate in combination with a silicone elastomer. The one to one mixture of these two materials is surprisingly a soft paste rather than the "rubbery" gel typical of the original silicone elastomer and it leaves a shiny film, not a matte film typical of the silicone elastomer. These changes are significant because the mixture is easier to incorporate in formulations than the silicone elastomer and yet it provides the unique film forming and feel properties of the silicone elastomer. Similarly, other polyurethane compounds can be mixed with the silicone elastomers to modify the various properties of the mixture such as tackiness, shine, viscosity and hydrophilicity.

DETAILED DESCRIPTION OF THE INVENTION

The following terms are used to describe the present invention. In instances where a term is not specifically defined herein, the term shall be given its meaning as understood by those of ordinary skill in the art.

The term "patient or subject" is used to describe a mammal, including a human to which compositions according to the present invention may be applied.

The term "personal care product" is used to describe a chemical composition used for the purpose of cleansing, conditioning, grooming, beautifying, or otherwise enhancing the appearance of the human body. Personal care products include skin care products, cosmetic products, antiperspirants, deodorants, perfume, toiletries, soaps, bath oils, feminine care products, hair-care products, oral hygiene products, depilatories, including shampoos, conditioners, hair straightening products and other hair care products, color cosmetics such as lipstick, creams, make-up, skin creams, lotions (preferably comprised of water-in-oil or oil-in-water emulsions), shave creams and gels, after-shave lotions and shave-conditioning compositions and sunscreen products, among numerous others.

Personal care products according to the present invention comprise an admixture or polymer of a silicone elastomer and polyurethane as otherwise described herein and an additional component selected from the group consisting of water, an aqueous solvent (e.g. alcohol or other compatible solvent), a non-aqueous solvent, emollients, humectants, oils (polar and non-polar) conditioning agents, surfactants, thickeners/thickening agents, stiffening agents, emulsifiers, medicaments, fragrances, preservatives, deodorant components, anti-perspirant compounds, skin protecting agents, pigments, dyes, coloring agents, sunscreens and mixtures thereof, among others.

Personal care products according to the present invention comprise about 0.01% to about 50% by weight of an admixture of a silicone elastomer and a polyurethane or a crosslinked silicone elastomer/polyurethane polymer, the remainder of the composition comprising at least one additional component selected from the group consisting of water, an aqueous solvent (e.g. alcohol or other water compatible solvent), a non-aqueous solvent, emollients, humectants, oils (polar and non-polar), conditioning agents, emulsifiers, surfactants, thickeners, stiffening agents, medicaments, fragrances, preservatives, deodorant components, anti-perspirant compounds, skin protecting agents, pigments, sunscreens and mixtures thereof, among others.

The term "silicone elastomer" describes a polyorganosiloxane polymer, which is generally crosslinked to produce a material that resembles rubber (resumes its original shape when a deforming force is removed). The elastomer according to the present invention may vary significantly in chemical composition but preferably is a polymeric composition comprised of units, where $R^2$ and $R^3$ are independently H, OH, $C_1$-$C_{10}$ (preferably $C_1$-$C_3$) alkyl, alkene or aryl groups and may vary in average molecular weight $M_n$ from about 1,000 to about 1,500,000 or more, preferably about 1,000 to about 100,000, more preferably about 2,500 to about 25,000 or more, depending upon the final viscosity and other characteristics desired. Silicone elastomers according to the present invention preferably contain at least one group which is capable of crosslinking with a functional group on a polyurethane polymer such as H, OH, $NH_2$, or an olefinic or other alkene group. For example, with silicone elastomers which contain an Si—H group, reaction with a free hydroxyl group on a polyurethane composition produces a crosslinked Si—O— polyurethane polymer group. In the case of a Si—OH group or Si—$NH_2$ group, reaction with an electrophilic group on a polyurethane compound such as an isocyanate, ester group (or activated ester) or other electrophilic group will result in a crosslinked silicone elastomer-polyurethane composition. In the case of a Si-alkene group, reaction with an olefinic group or other activated group on the polyurethane (through dimethylsilicone hydride groups that are contained on a separate crosslinking silicone polymer) can produce a silicone elastomer-polyurethane polymer crosslinked through the double bonds on each of the elastomer and polyurethane. Alternatively, the silicone elastomer and polyurethane may simply be admixed without further crosslinking/polymerization.

In preferred aspects of the present invention, the silicone elastomer comprises about 0.25% to about 99.75% by weight of the admixture of elastomer and polyurethane wherein the elastomer and polyurethane may be covalently linked (crosslinked) or uncrosslinked in admixture, preferably about 1.0% to about 99% by weight of the admixture, about 1.5% to about 98.5% by weight of the admixture, about 5% to about 95% by weight, about 10% to about 90% by weight, about 20% to about 80% by weight, about 25% to about 75% by weight, about 30% to about 70% by weight, about 35% to about 65% by weight, about 40% to about 60% by weight, about 45% to about 55% by weight, about 50% to about 50% by weight.

In certain preferred embodiments, containing silicone elastomers according to the present invention, the silicone elastomer has the following structure:

Where $R^1$ and $R^a$ are independently H, an optionally substituted $C_1$-$C_6$ alkyl group (substitution with OH or a $C_1$-$C_3$ alkyl group which itself may be optionally substituted with a hydroxyl group) or an optionally substituted $C_2$-$C_6$ alkenyl group (which term may include an acrylate or methacrylate group);

Each $R^2$ and $R^3$ is independently H, OH, or a $C_1$-$C_3$ alkyl group; and n is from 5 to 50,000, about 10 to about 25,000, about 100 to about 10,000.

Additional preferred silicone elastomer compounds for use in the present invention have the following structure:

Where $R^1$ and $R^a$ are independently H, an optionally substituted $C_1$-$C_6$ alkyl group (substitution with OH or a $C_1$-$C_3$ alkyl group which itself may be optionally substituted with a hydroxyl group) or an optionally substituted $C_2$-$C_6$ alkenyl group (which term may include an acrylate or methacrylate group);

Each $R^2$ and $R^3$ is independently H, OH, or a $C_1$-$C_3$ alkyl group (preferably a $C_1$-$C_3$ alkyl group, preferably a methyl group), preferably $R^2$ and $R^3$ are both $C_1$-$C_3$ alkyl groups, preferably both are the same $C_1$-$C_3$ alkyl group, preferably methyl groups;

Each $R^{2a}$ and $R^{3a}$ is independently H, OH, or a $C_1$-$C_3$ alkyl group, preferably at least one of $R^{2a}$ or $R^{3a}$ is H and the other is a $C_1$-$C_3$ alkyl group;

n is from 5 to 50,000, about 10 to about 25,000, about 100 to about 10,000, about 100 to 5,000; about 500 to 5,000; about 500 to about 2,500; about 100 to about 1,000, about 150 to about 1,000; and j is from 0 to 50, preferably 1 to about 25, about 1 to 4, about 2 to 15 about 3 to 10; about 5 to 10.

Other preferred silicone elastomers for use in the present invention include polyorganosiloxane polymers which are crosslinked with a polysiloxane (e.g., end-capped with reactive Si—H groups which react with double bonds on the uncrosslinked polysiloxane polymer) crosslinking agent. Silicone elastomers generally range in size from an average molecular weight of at least about 500 to upwards of several million or more, more preferably about 2000 to about 1,000,000, more preferably about 5,000 to about 500,000. Silicone elastomers are generally formed by reacting a polysiloxane polymer which contains at least one side chain comprising a hydrocarbon which contains at least one reactive double bond (e.g. a vinyl group or an allyl group) which is reactive with an Si—H bond. The crosslinker may vary in size, but generally ranges in size from a molecular weight of about 125 to several thousand or more, with a preferred molecular weight range of about 200 to about 750.

Preferred silicone elastomers according to the present invention include for example, the silicone elastomers which are disclosed in U.S. Pat. No. 6,936,686, which is incorporated by reference in its entirety herein.

The term "polyurethane" shall mean, within the context of its use, a polymeric urethane compound comprising at least one and preferably, two or more urethane linkages which are generally formed by reacting at least one compound containing a free alcohol (primary, secondary or tertiary), preferably at least one compound containing at least two alcohol groups ("polyol") and a diisocyanate compound. Thus, the term polyurethane as used herein incorporates dimer urethanes (those compounds which contain a single urethane bond) which are formed from a monohydric alcohol of varying structure, which structure may contain, for example, an active group or a protected active group such as a silyl-protected hydroxyl group or amine group wherein the protecting may be removed subsequent to formation of the polyurethane or an olefinic group (such as for example, a vinyl group, acrylate or methacrylate group) which can participate in a reaction with a group from the silicone elastomer to produce a crosslinked silicone elastomer/polyurethane composition. In addition, polyurethanes according to the present invention are formed by reacting at least one polyol (a compound which is either hydrocarbon or siloxane based and which contains at least two free alcohol groups) with a diisocyanate to produce a polyurethane, with the polyol optionally and preferably containing at least one functional group which does not participate in the polymerization reaction to form the polyurethane composition, but which, subsequent to the polymerization reaction, can be used to crosslink the polyurethane composition to a silicone elastomer in preferred compositions according to the present invention.

Preferred urethane polymers according to the present invention have the general structure:

Where $R^5$ is an optionally substituted hydrocarbon or optionally substituted siloxane group, preferably, an optionally substituted $C_1$-$C_{50}$ hydrocarbon group, optionally containing at least one olefinic group, or preferably a siloxane group according to the structure:

$R^{5a}$ is an optionally substituted hydrocarbon or a siloxane group, preferably, an optionally substituted $C_1$-$C_{50}$ hydrocarbon group, optionally containing at least one olefinic group, or a siloxane group according to the structure:

Wherein Y is absent, O or a group;
X is absent or a group;
X' is absent or a group;
Y' is absent or a group;
W is absent when r is an integer of 1 or more and W is absent or O when r is 0;
Q is absent or O;
q is an integer from 0 to 10, preferably 1 to 6, preferably 1 to 3;
r is an integer from 0 to 100, 0 to 40, preferably 1 to 20 or 1 to 10, with the proviso that q or r is at least 1;
T is absent or O;
W' is absent when r is 0 and is a Z group when r is 1 or more;
$W^2$ is H;
Z is independently an ethylene group, a propylene group or a mixture of ethylene and propylene groups;
$R^{2b}$ and $R^{3b}$ are each independently H or a $C_1$-$C_3$ alkyl group (preferably a $C_1$-$C_3$ alkyl group, preferably a methyl group), preferably $R^2$ and $R^3$ are both $C_1$-$C_3$ alkyl groups, preferably both are the same $C_1$-$C_3$ alkyl group, preferably methyl groups;
$R^{2c}$ and $R^{3c}$ are independently selected from H, an optionally substituted $C_1$-$C_6$ alkyl group (substitution with OH or a $C_1$-$C_3$ alkyl group which itself may be optionally substituted with a hydroxyl group) or an optionally substituted $C_2$-$C_6$ alkenyl group (which alkenyl may include an acrylate or methacrylate group);
R' is an optionally substituted $C_2$ through $C_{36}$ (preferably, $C_6$ through $C_{22}$, most preferably an isophorone group) linear, cyclic or branch-chained saturated or unsaturated hydrocarbon group (which may be monomeric or dimeric, an aromatic group, including a phenyl or benzyl group or substituted phenyl or benzyl group, an alkylphenyl, alkylbenzyl or substituted alkylphenyl or alkylbenzyl group);
i is 0, 1, 2, 3, 4, 5 (preferably 0 or 1);
k is an integer from 0 to 100, 1 to 100, about 5 to 50, about 10 to 45, preferably about 20 to 40; and
m is from 1 to 100,000, about 1 to 25,000, about 5 to 25,000, about 50 to 20,000, about 50 to 20,000, about 100 to 20,000, about 100 to 10,000, about 200 to 5,000, about 250 to 2,500, about 500 to about 2,000, 1 to about 1,000, 1 to about 750, 2 to about 650, about 50 to 15,000, about 10 to 10,000, about 200 to 5,000, about 250 to about 2,500, about 5 to about 150, about 3 to 100, about 5 to 250. Preferably, the polyurethane according to the present invention is obtained by reacting a polyol (which may be hydrocarbon based or siloxane based and contains at least two hydroxyl groups) with a diisocyanate compound to produce a polyurethane composition accordingly.

In certain preferred aspects, $R^5$ is a O—$R^6$ group and $R^{5a}$ is a $R^6$—OH group where $R^6$ is a optionally substituted hydrocarbon or an optionally substituted siloxane group as set forth and generally described above.

One or more polyols and/or diisocyanates may be used to produce polyurethane polymers according to the present invention, with preferred polyols having, in addition to at least two free alcohol groups to participate in polymerization reactions to form polyurethanes, at least one additional reactive functional group which can serve to crosslink silicone elastomers in the present invention, and with the diisocyanate preferably being isophorone diisocyanate.

Preferred polyurethanes according to the present invention also are prepared from a diisocyanate, preferably isophorone diisocyanate and castor oil, glycerin and glycerin esters, propylene glycol and its esters, dipropylene glycol and its esters, alkyl amines, ethoxylated alkyl amines, propoxylated alkyl amines, silicone ethoxylates and silicone propoxylates, among others.

Figure 1:
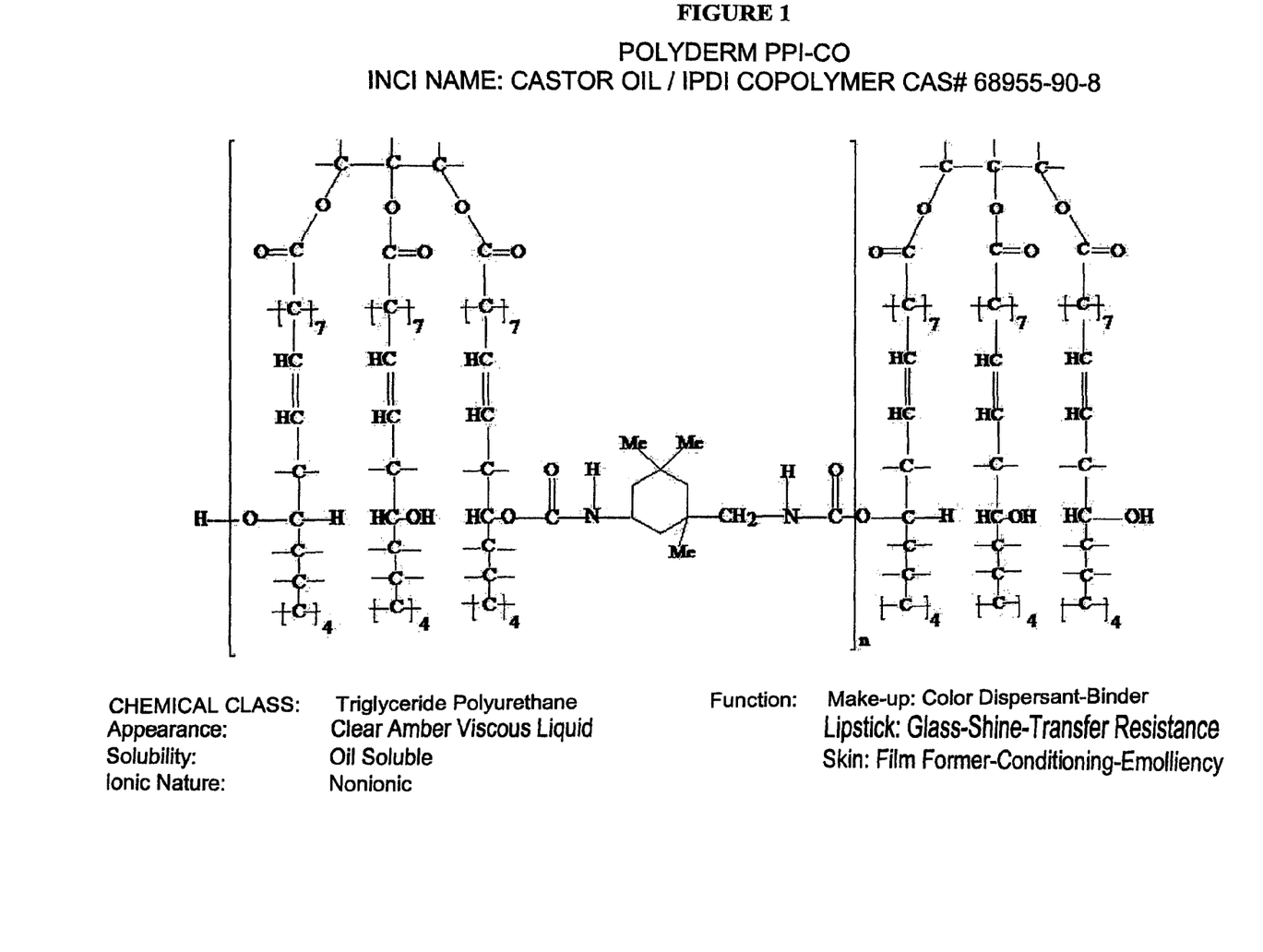
FIG. 1 shows the polyurethane composition Polyderm PPI-CO (Castor oil/IPDI copolymer), which is obtained by reacting castor oil with isophororone diisocyanate.
Figure 2:
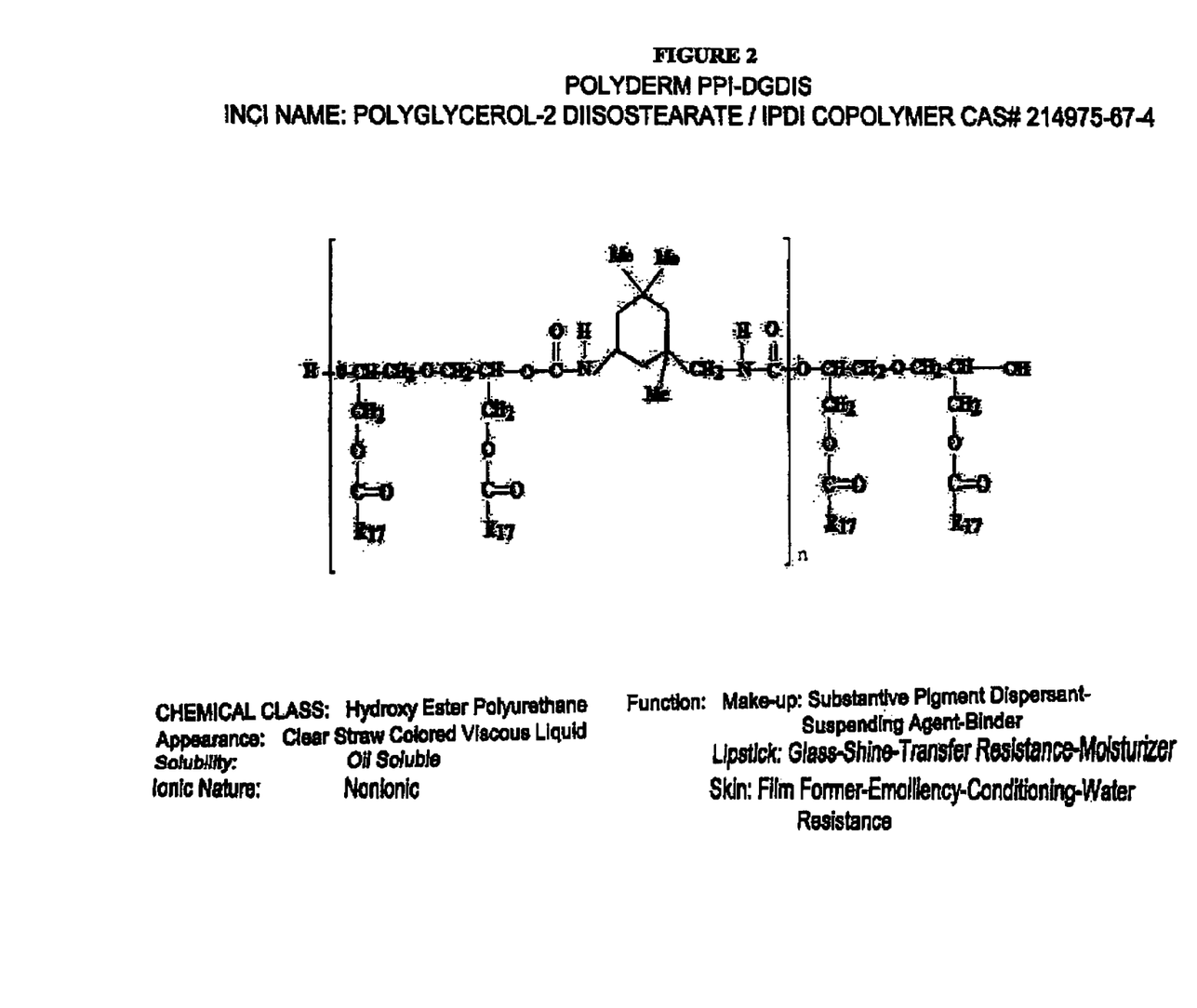
FIG. 2 shows the polyurethane composition Polyderm PPI-DGDIS (Polyglycerol-2-Diisostearate/IPDI copolymer).
Figure 3:
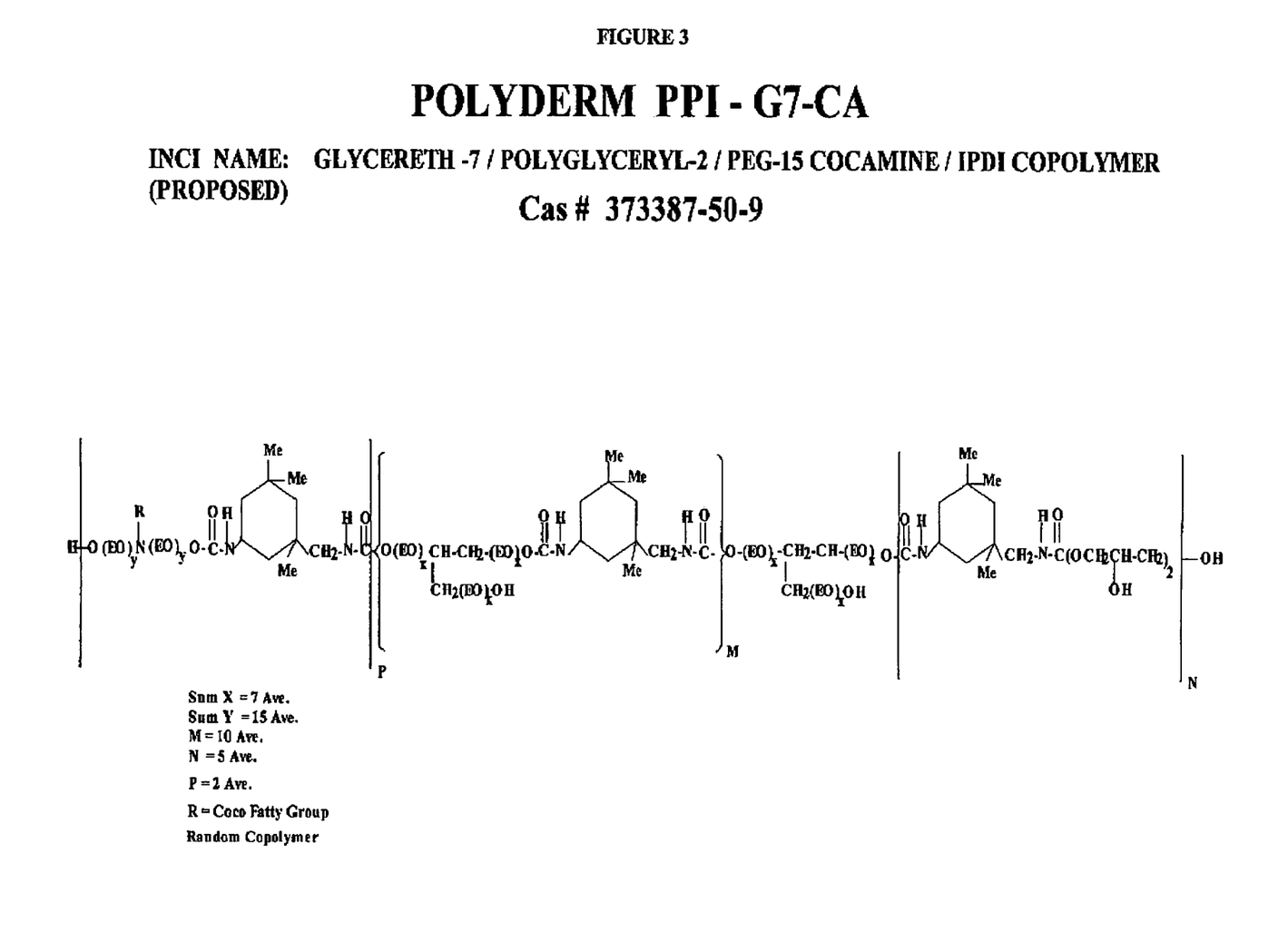
FIG. 3 shows the polyurethane composition Polyderm PPI-G7-CA (Gycereth-7/Polyglyceryl-2/PEG-15 Cocamine/IPDI Copolymer) wherein x is 7 avg., y is 8 avg., z is 3 avg, m is 10 avg, and n is 5 avg.
Figure 4:
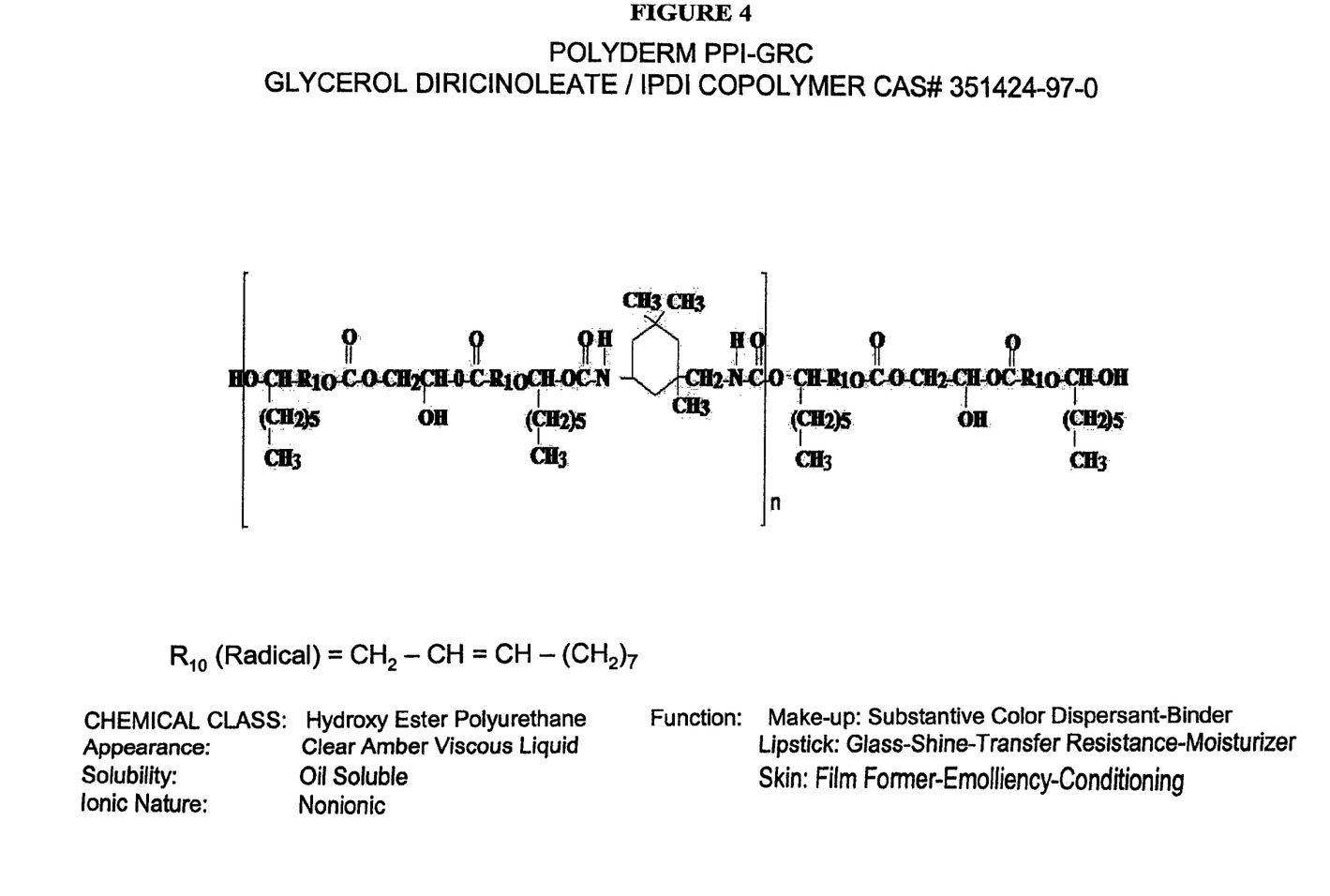
FIG. 4 shows the polyurethane composition Polyderm PPI-GRC (Glycerol Diricinoleate/IPDI Copolymer). $R_{10}$ is a —$CH_2$—CH=CH—$(CH_2)_7$ radical and n is 5 to 100.
Figure 5:
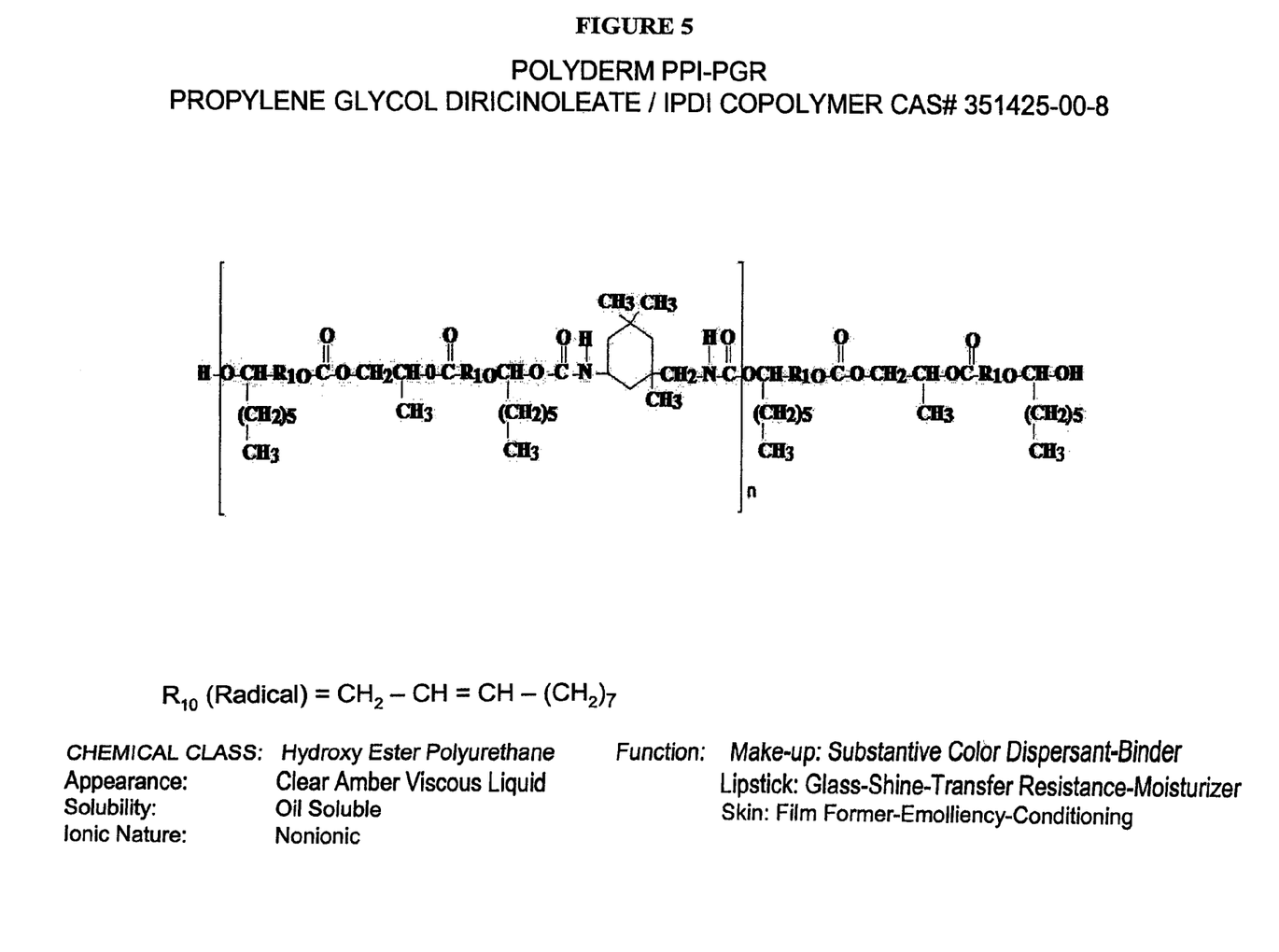
FIG. 5 shows the polyurethane composition Polyderm PPI-PGR (Propylene Glycol Diricinoleate/IPDI Copolymer). $R_{10}$ is a —$CH_2$—CH=CH—$(CH_2)_7$ radical and n is 5 to 100.
Figure 6:
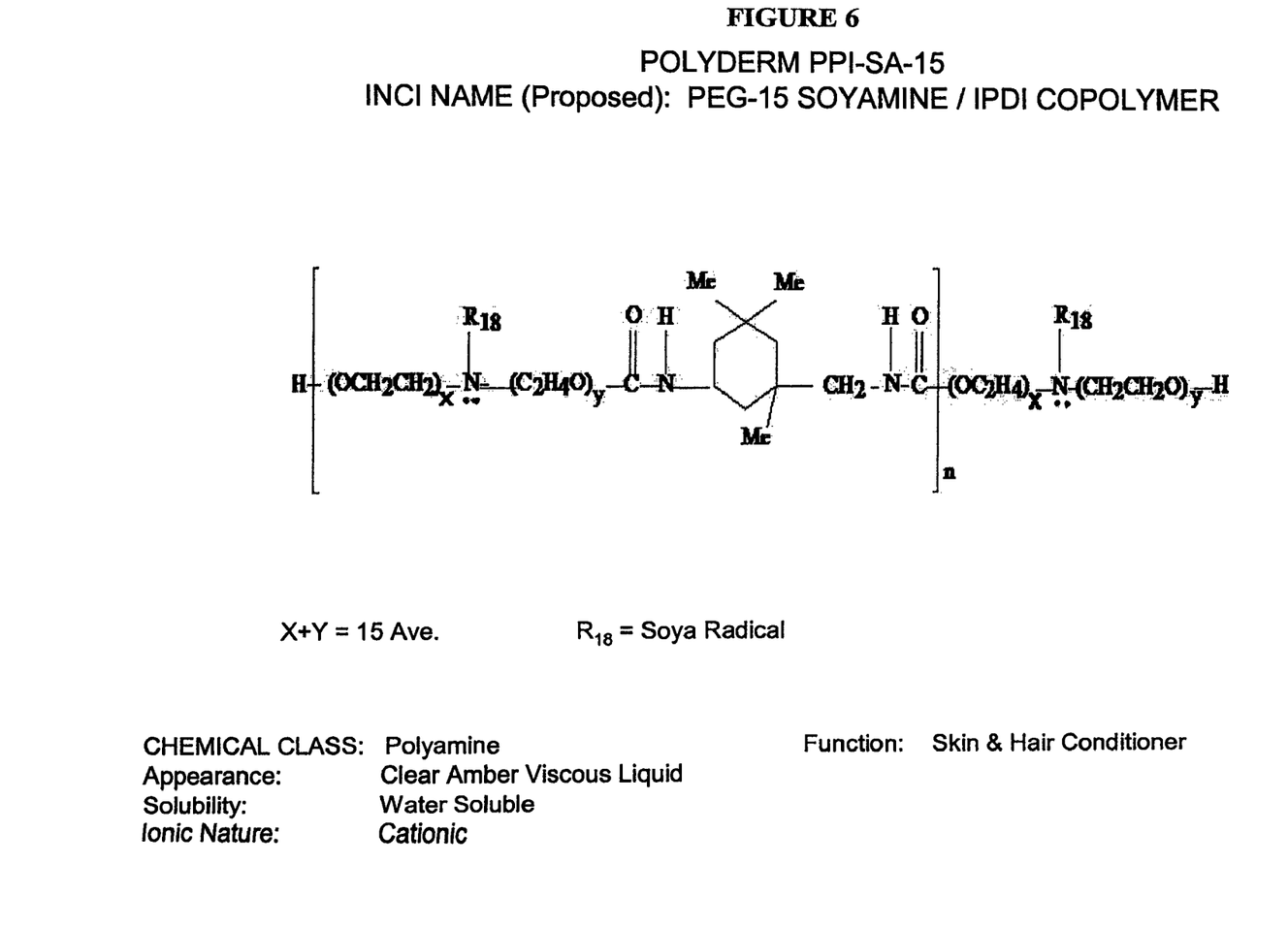
FIG. 6 shows the polyurethane composition Polyderm PPI-SA-15 (PEG-15 Soyamine/IPDI Copolymer). R+Y is an average of 15. $R_{18}$ is a soya radical and n is 5 to 100.
Figure 7:
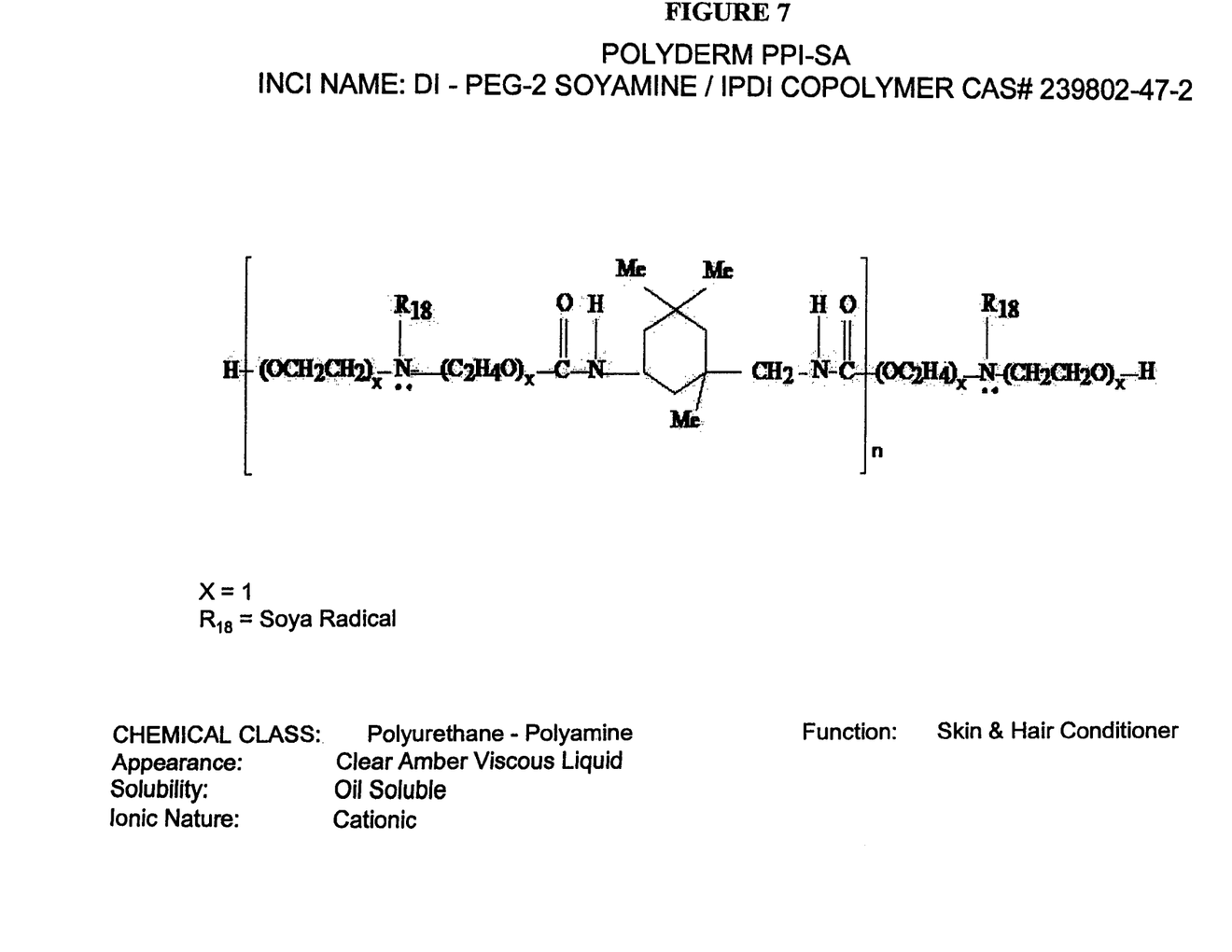
FIG. 7 shows the polyurethane composition Polyderm PPI-SA (Di-PEG-2 Soyamine/IPDI Copolymer). X is 1. $R_{18}$ is a soya radical and n is 5-100.
Figure 8A:
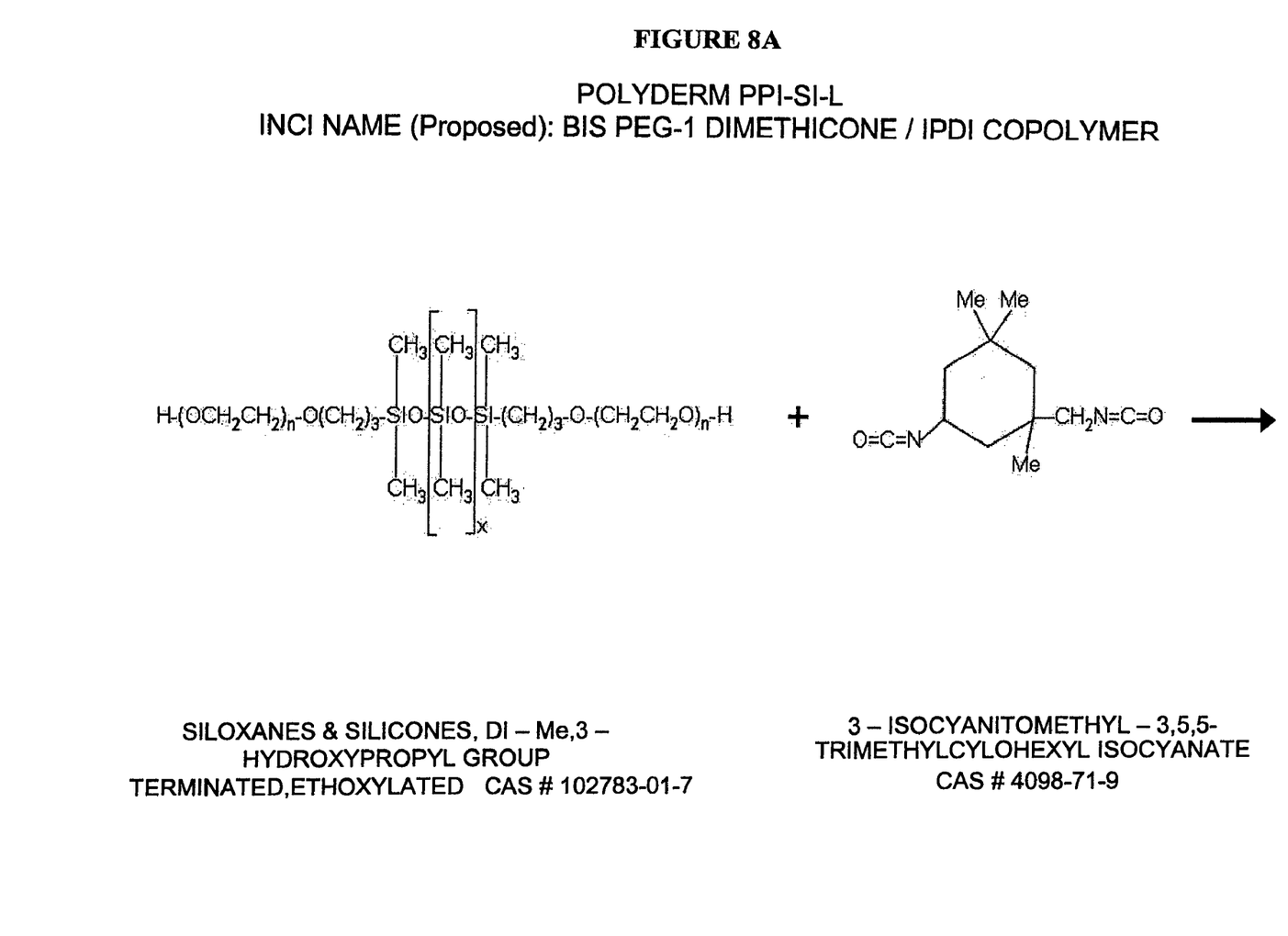
FIG. 8 shows the polyurethane composition Polyderm PPI-SI-L (BIS PEG-1 Dimethicone/IPDI Copolymer.
Figure 8B:
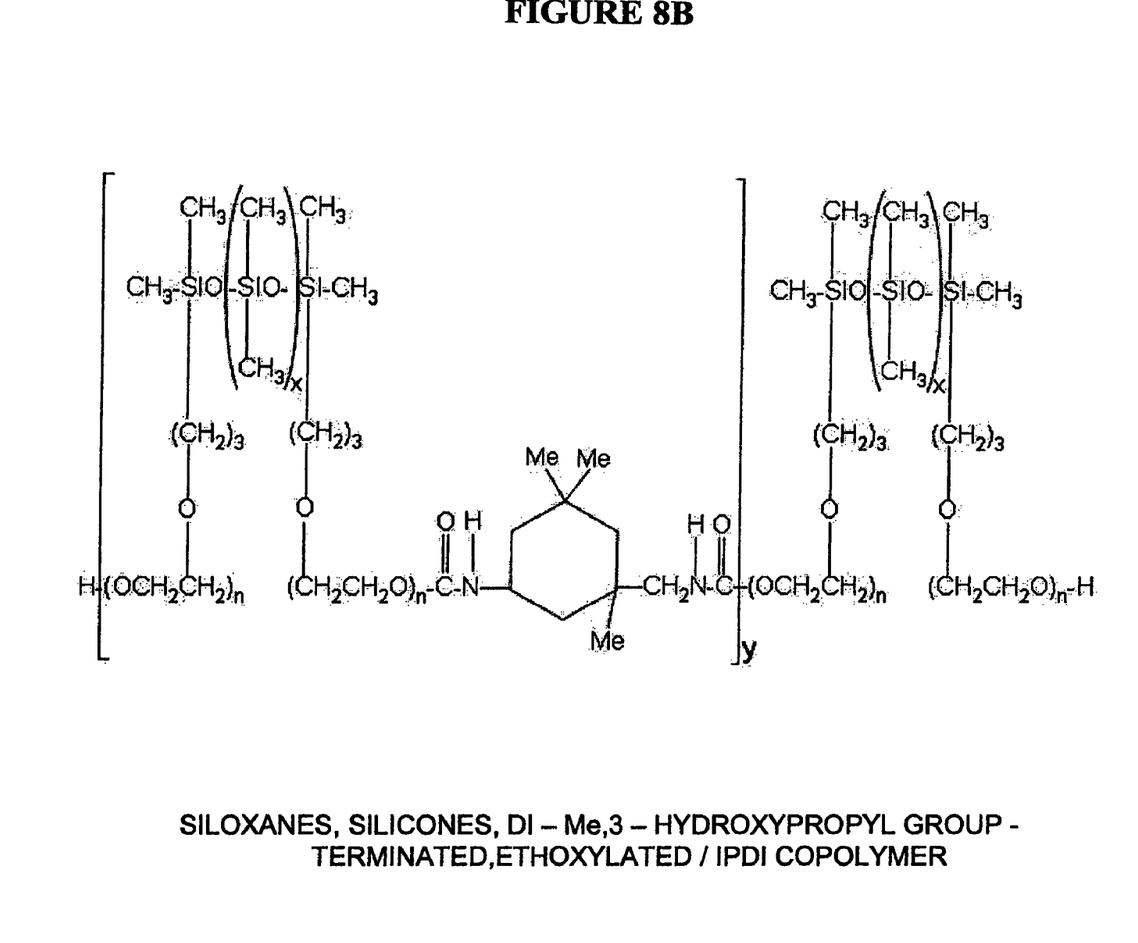

Preferred polyurethane compositions for use in the present invention include the various polyurethane compositions which are disclosed in FIGS. 1-8 hereof, which are available commercially from Alzo International, Inc. of Sayreville, N.J., USA.

The term "polyol" refers to a hydrocarbon or siloxane based compound having at least two free hydroxyl groups which can participate in a reaction with diisocyanate to provide a polyurethane composition. In preferred aspects of the invention, a polyol according to the present invention, in addition to the two free hydroxyl groups which react with diisocyanate compounds, also contains an additional "reactive functional group" which, subsequent to the formation of the polyurethane compound, may participate in a crosslinking reaction with a reactive functional group on a silicone elastomer admixed with the polyurethane, to produce crosslinked silicone elastomer/polyurethane compositions The term "monohydric alcohol" refers to a compound containing a single hydroxyl group which may react with a diisocyanate compound to produce dimer urethane compounds according to the present invention. Monohydric alcohols advantageously contain at least one reactive functional group which, after formation of the dimer urethane, can react with a reactive group on a silicone elastomer admixed with the dimer urethane to produce a crosslinked silicone elastomer/polyurethane compositions.

The polyol(s) used to polymerize with diisocyanate may vary widely in character from hydrophilic (polar) to hydrophobic non-polar. Although a large number of polyols can be used to produce polyurethane compositions according to the present invention, preferred polyols include triglycerides which contain fatty acids having free hydroxyl groups and/or olefinic groups such as castor oil triglycerides or other triglycerides, glycerol, substituted glycerols or polyglycerols such as $C_{10}$-$C_{24}$ di-fatty polyglycerol (preferably, polyglycerol-2-diisostearate), di-fatty alkanolmonoglycerol, such as glycerol diricinoleate, polyethylene glycol alkylamines, especially polyethyleneglycol fatty amines, such as PEG-15 cocamine, or di-PEG-15 soyamine or related dipolyethylene glycol fatty amines, including di-PEG soyamine, polyethyleneglycol, substituted polyethyleneglycol, such as propyleneglycol diricinoleate, polydialkylsiloxane such as polydimethylsiloxane (e.g. dimethicone), or a di-polyethyleneglycol dimethicone, or related polysiloxane. Polyols are polymerized with a diisocyanate compound, preferably isophorone diisocyanate.

The term "diisocyanate" is used throughout the specification to describe a linear, cyclic or branch-chained hydrocarbon having two free isocyanate groups. The term "diisocyanate" also includes halogen substituted linear, cyclic or branch-chained hydrocarbons having two free isocyanate groups. Exemplary diisocyanates include, for example, isophoronediisocyanate, m-phenylene-diisocyanate, p-phenylenediisocyanate, 4,4-butyl-m-phenylene-diisocyanate, 4-methoxy-m-phenylenediisocyanate, 4-phenoxy-m-phenylenediisocyanate, 4-chloro-m-phenyldiisocyanate, toluene diisocyanate, m-xylylene diisocyanate, p-xylylene diisocyanate, 1,4-napthalene diisocyanate, cumene-1,4-diisocyanate, durene diisocyanate, 1,5-napthylene diisocyanate, 1,8-napthylene diisocyanate, 1,5-tetrahydronapthylene diisocyanate, 2,6-napthylene diisocyanate, 1,5-tetrahydronapthylene diisocyanate; p,p-diphylene diisocyanate; 2,4-diphenylhexane-1,6-diisocyanate; methylene diisocyanate; ethylene diisocyanate; trimethylene diisocyanate, tetramethylene diisocyanate, pentamethylene diisocyanate, hexamethylene diisocyanate, nonamethylene diisocyanate, decamethylene diisocyanate, 3-chloro-trimethylene diisocyanate and 2,3-dimethyltetramethylene diisocyanate, among numerous others. Isophorone diisocyanate is the preferred diisocyanate used in the present invention.

Polyurethane compounds used in the present invention are prepared by well known methods in the art. A general scheme involves reaction of at least about two moles of a monohydric alcohol or at least about one mole of (purchased commercially or prepared using well known methods in the art) polyol with at least one mole of a diisocyanate in the presence of heat and either an amine or tin catalyst such as stannous octanoate. Each isocyanate moiety is thereby converted to a urethane moiety while maintaining the presence of "free and unreacted" reactive functional groups which may be later used to crosslink the silicone elastomer in admixture. Heat is maintained until a suitable acid number is attained and the reaction mass is cooled, washed, neutralized dried and distilled if necessary. The product should be essentially odorless, essentially water-white in color and contain a substantial absence of free fatty acid or residual catalyst.

The polyurethane and silicone elastomer are admixed together to produce a silicone elastomer/polyurethane composition. Alternatively and preferably, a silicone elastomer containing at least one functional reactive group (e.g., Si—H, Si—OH, $NH_2$, Si—C=C group) is admixed with a polyurethane also containing at least one reactive functional group (OH, $NH_2$, olefin (vinyl) or acrylate or methacrylate group and then reacted to provide a crosslinked silicone elastomer/polyurethane polymeric material, having varied viscosity, but preferably being presented as a gel. The silicone elastomer and polyurethane are reacted without solvent or in the presence of solvent according to the nature of the reactive functional group on the silicone elastomer and the polyurethane and the type of reaction which produces a crosslinked product, where applicable. The reactions may be conducted at temperatures at (ambient) or below room temperature, but preferably the reactions occur at elevated temperatures alone or in the presence of a catalyst or acid scavenger (such as triethyl amine, etc.). The resulting crosslinked silicone elastomer/polyurethane polymer (especially the final viscosity) may vary according to the reaction conditions chosen to effect the crosslinking reaction.

The silicone elastomer/polyurethane admixture/polymer prepared above may be added to a number of components to product favorable characteristics in personal care products, including skin care products, cosmetic products, antiperspirants, deodorants, perfume, toiletries, soaps, bath oils, feminine care products, hair-care products, oral hygiene products, depilatories, including shampoos, conditioners, hair straightening products and other haircare products, color cosmetics such as lipstick, creams, make-up, skin creams, lotions and sunscreen products, among numerous others.

Compounds of the present invention may be used as emollients for the skin and epithelial tissue such as hair, ungual tissue (nails), skin and related mucous membranes, especially given the combined attributes of emolliency (from the silicone elastomer) and skin adherence, viscosity enhancement and favorable skin interaction (generally) and wettability and other attributes (which can be formulated into the polymer depending upon which polyurethane is chosen). By addition of an effective amount of the present compositions, formulations for use as personal care products, including cosmetic and toiletry products will acquire a soothing and favorable interaction which promotes skin adherence, moisturization, wettability and favorable viscosity attributes of the final personal care formulation. In addition, because the size of the silicone elastomer and polyurethane can be varied substantially, numerous personal care products ranging from lotions and creams to thickened formulations to be used in stick deodorants and related products can be readily formulated.

Effective amounts of the present compounds may also serve a dual function, for example, as gloss-producing agents for lipsticks and lip balm formulations in the personal care, cosmetic and toiletry industries as a substitute(s) for castor oil normally used in such formulations, especially where the polyurethane is made from castor oil. The compounds of the present invention exhibit outstanding solubility characteristics for pigments used in lip products and are compatible with existing raw materials used in lip formulations such as castor oil, triglycerides of caprylic/capric acids, triglyceride of caprylic acid, mixtures of octyl isononanoate/diethylene glycol/dioctanoate and dioctanoate/isodecyl octanoate, among others.

The term "effective amount" is used throughout the present specification to describe concentrations or amounts of compounds according to the present invention which, when used in context, are effective in conveying desired traits such as emolliency, wettability, skin adherence, storage stability, and/or solubility to a formulation of a personal care product or are used to produce a compound or composition according to the present invention.

The term "unsubstituted" is used to describe a hydrocarbon moiety such as an alkyl group or alkene or related unsaturated group which contains only hydrogen atoms bonded to carbons within the moiety. It can include aryl (aromatic groups such as substituted phenyl) groups, as well. The term "substituted" is used to describe a hydrocarbon moiety which contains, within the context of its use, a pendant hydroxyl group, an ether group (such as within a glycol or polyglycol, glycerol or polyglycerol or other group), a keto group, an amine (which may itself be substituted with alkyl groups, including fatty ($C_8$-$C_{30}$) alkyl groups or alkanol groups, for example), an alkyl or alkene group attached to a carbon atom of the moiety. The number of carbon atoms within a substituent group may vary from 0 to 30 or more, 0 to 24 or more, 0 to 18, 0 to 12, 0 to 10, 1 to 8, and 1 to 6 and may contain 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more carbon atoms, depending upon the context of the use of the compound to which the substituent is attached.

The term "oil" is used throughout the specification to describe any of various lubricious, hydrophobic and combustible substances obtained from animal, vegetable and mineral matter. Emollient oils for use in the present invention may include petroleum-based oil derivatives such as purified petrolatum and mineral oil. Petroleum-derived oils include aliphatic or wax-based oils, aromatic or asphalt-based oils and mixed base oils and may include relatively polar and nonpolar oils. "Non-polar" oils are generally oils such as petrolatum or mineral oil or its derivatives which are hydrocarbons and are more hydrophobic and lipophilic compared to synthetic oils, such as esters, which may be referred to as "polar" oils. It is understood that within the class of oils, the use of the terms "non-polar" and "polar" are relative within this very hydrophobic and lipophilic class, and all of the oils tend to be much more hydrophobic and lipophilic than the water phase which is used to produce the water-in-oil emulsion of the present invention. Preferred hydrophobic oils for use in the present invention include mineral oil and petrolatum. Preferred less hydrophobic (i.e., more polar) oils for use in the present invention include a number of maleates, neopentanoates, neopentanoyls, citrates and fumarates, and any other cosmetically acceptable ester emollient.

In addition to the above-described oils, certain essential oils derived from plants such as volatile liquids derived from flowers, stems and leaves and other parts of the plant which may include terpenoids and other natural products including triglycerides may also be considered oils for purposes of the present invention.

Petrolatum (mineral fat, petroleum jelly or mineral jelly) and mineral oil products for use in the present invention may be obtained from a variety of suppliers. These products may range widely in viscosity and other physical and chemical characteristics such as molecular weight and purity. Preferred petrolatum and mineral oil for use in the present invention are those which exhibit significant utility in cosmetic and pharmaceutical products. Cosmetic grade oils are preferred oils for use in the present invention.

Additional oils for use in the present invention may include, for example, mono-, di- and tri-glycerides which may be natural or synthetic (derived from esterification of glycerol and at least one organic acid, saturated or unsaturated, such as for example, such as butyric, caproic, palmitic, stearic, oleic, linoleic or linolenic acids, among numerous others, preferably a fatty organic acid, comprising between 8 and 26 carbon atoms). Glyceride esters for use in the present invention include vegetable oils derived chiefly from seeds or nuts and include drying oils, for example, linseed, iticica and tung, among others; semi-drying oils, for example, soybean, sunflower, safflower and cottonseed oil; non-drying oils, for example castor and coconut oil; and other oils, such as those used in soap, for example palm oil. Hydrogenated vegetable oils also may be used in the present invention. Animal oils are also contemplated for use as glyceride esters and include, for example, fats such as tallow, lard and stearin and liquid fats, such as fish oils, fish-liver oils and other animal oils, including sperm oil, among numerous others. In addition, a number of other oils may be used, including $C_{12}$ to $C_{30}$ (or higher) fatty esters (other than the glyceride esters, which are described above) or any other acceptable oil.

In general, compositions according to the present invention are included in personal care products/formulations in effective amounts, i.e., amounts which produce an intended effect. The amount of composition generally ranges from about 0.01% to about 50% by weight or more of personal care formulations according to the present invention. Alternatively, compositions according to the present invention may be included in final personal care compositions in amounts ranging from about 0.05% to about 45% by weight, about 0.1% to about 40% by weight, about 0.25% to about 30% by weight, about 0.25% to about 20% by weight, about 0.5% to about 15% by weight, about 0.75% to about 10% by weight, about 1% to about 7.5% by weight, about 1% to about 5% by weight and about 1% to about 3% by weight of the final personal care composition.

In preferred embodiments of emulsion-based formulations (wherein the formulation comprises an oil, water, an emulsifier and the present composition, compositions according to the present invention are included in amounts ranging from about 0.1% to about 7.5% by weight. In the case of shampoos and conditioners, compositions according to the present invention are included in amounts ranging from about 0.1% to about 3% by weight of the formulation. We can (and have) used amounts up to about 20% to 25% in shampoos and conditioners.

For example, in haircare products, such as shampoos, rinses, conditioners, hair straighteners, hair colorants and permanent wave formulations, the compositions according to the present invention preferably comprise about 0.1% to about 20% by weight, more preferably about 0.25% to about 5% by weight of the final end-use hair-care composition. Other components which may be included in hair-care formulations include, for example, a solvent or diluent such as water and/or alcohol, other surfactants, emulsifiers, thickeners, coloring agents, dyes, preservatives, additional conditioning agents and humectants, among numerous others.

In the case of shave creams and gels, after-shave lotions and shave-conditioning compositions (for example, pre-electric shave formulations), the compositions according to the present invention are included in amounts ranging from about 0.25% to about 15% or more by weight, more preferably about 0.5% to about 10% by weight. Other components which may be included in these end-use compositions include, for example, water, and at least one or more of emollients, humectants and emulsifiers, thickeners and optionally, other conditioning agents, medicaments, fragrances and preservatives.

In the case of skin lotions and creams, the present compositions are included in amounts ranging from about 0.25% to about 15% by weight, more preferably, about 0.5 to about 10% by weight. Additional components which may be employed in these compositions include, for example, water, emollients and emulsifiers, surfactants, oils, and optionally, other conditioning agents, thickeners, medicaments, fragrances and preservatives.

In the case of sunscreens and skin-protective compositions, the present compositions are included in amounts ranging from about 0.25% to about 15% or more by weight, preferably about 0.5% to about 7.5% by weight of the final formulations. Additional components which may be employed in these compositions may include, for example, a UV absorbing composition such as para-amino benzoic acid (PABA) or a related UV absorber or a pigment such as $TiO_2$ and optional components including, for example, one or more of an oil, water, suspending agents, other conditioning agents and emollients, among others.

In the case of bar and liquid soaps, compositions according to the present invention are included in amounts ranging from about 0.25% to about 20% by weight or more, preferably about 0.5% to about 10% by weight. Additional components which may be included in bar and liquid soaps include water and surfactants and optionally, bactericides, fragrances and colorants, among others.

Other personal care products, not specifically mentioned, generally comprise about 0.1% to about 50% by weight of a composition according to the present invention and other components of personal care products as otherwise set forth in detail herein.

EXAMPLES

The following examples are illustrative of the product concepts, and are intended to provide formulas and manufacturing methods and that show some of the variations and applications that are possible.

| Ingredients | Example 1 % w/w | Example 2 % w/w | Example 3 % w/w |
|---|---|---|---|
| Silicone Elastomer (D5-6) | 99.0 | 50.0 | 1.0 |
| Polyderm PPI CO | 1.0 | 50.0 | 99.0 |
|  | 100.0 | 100.00 | 100.00 |

The Silicone Elastomer D5-6 is made per U.S. Pat. No. 6,936,686, from a polyorganohydrosiloxane of about 3500 to 4000 molecular weight and with 6 to 7 hydrosilane groups per molecule reacted with a 20,000 to 25,000 molecular weight vinyl terminated polydimethylsiloxane in a reaction medium of cyclopentasiloxane at ~12% w/w concentration. After polymerization, the elastomer concentration is reduced to 6% w/w by the addition of cyclopentasiloxane (D5). The Polyderm PPI CO is made per U.S. Pat. No. 5,707,612 and is a polyurethane that is prepared from isophorone diisocyanate and castor oil. The mixtures made in the examples are intended to span a wide range of product concentrations in order that we can better understand the variation in properties with an eye to their applications in personal care products. All of the examples are made by weighting the components and dispersing the ingredients with good mechanical (propeller) mixing until uniform.

Example 1 is a hazy/cloudy soft smooth gel with no visible particles or separations that forms stable peaks when displaced and will just flow when stirred. These properties are the same as those of the parent silicone elastomer gel (D5-6) used in the mixture except that the original silicone elastomer gel is transparent, clear and water white. Example 2 is also hazy/cloudy but it is pale yellow in color and is much more paste-like in appearance. It flows when stirred and leaves a shiny, oily feeling slightly tacky film on skin. The film is not as tacky or as oily feeling as a film formed from Polyderm PPI CO itself, but it is "waterproof" and sheds water readily. Example 3 is a light amber colored viscous liquid with white particles floating in it. It is Polyderm PPI CO with "chunks" of silicone elastomer floating in it. The properties are those of Polyderm PPI CO liquid. Evidently there is a concentration between 50/50 and 99/1 at which the Polyderm PPI CO and the silicone elastomer become incompatible. Example 2 shows the most utility, finding applications in lip stick and lip gloss formulas where shine and durable film formation are desirable properties.

| Ingredients | Example 4 % w/w | Example 5 % w/w | Example 6 % w/w |
|---|---|---|---|
| Silicone Elastomer (D5-6) | 99.0 | 50.0 | 1.0 |
| Polyderm PPI DGDIS | 1.0 | 50.0 | 99.0 |
|  | 100.0 | 100.00 | 100.00 |

These examples are mixtures made from Polyderm PPI DGDIS which is a polyurethane made from isophorone diisocyanate and diglyceryl diisostearate and the same silicone elastomer D5-6 that was used in the previous examples. Polyderm PPI DGDIS is used in cosmetics to provide shine and it has a noticeable stickiness. Example 4 is a very thick, hazy/cloudy gel that flows when stirred and its properties are similar to those of the bulk silicone elastomer. It applies smoothly to skin leaving a matte, extremely smooth low friction film. Example 5 shows signs of separation and has a small clear layer on the bottom after 3 months storage at room temperature. It is a viscous opaque liquid that applies smoothly on skin leaving a durable, water resistant shiny film. Example 6 is a light amber colored viscous liquid with white particles floating in it. It is Polyderm PPI DGDIS with silicone elastomer particles floating in it. The properties are those of Polyderm PPI DGDIS liquid. Evidently there is a concentration between 50/50 and 99/1 at which the Polyderm PPI CO and the silicone elastomer become incompatible. Example 5 shows the most utility, finding applications in lip stick and lip gloss formulas where shine and durable film formation are desirable properties. This combination has less tack than the Polyderm PPI DGDIS and forms a film that has about the same shine as Polyderm PPI DGDIS.

| Ingredients | Example 7 % w/w | Example 8 % w/w | Example 9 % w/w |
|---|---|---|---|
| Silicone Elastomer (D5-6) | 99.0 | 50.0 | 1.0 |
| Polyderm PPI PGR | 1.0 | 50.0 | 99.0 |
|  | 100.0 | 100.00 | 100.00 |

These examples are mixtures made from Polyderm PPI PGR which is a polyurethane made from isophorone diisocyanate and propylene glycol ricinoleate and the same silicone elastomer D5-6 that was used in the previous examples. Polyderm PPI PGR is used as a film former in cosmetics and it has high shine very high tack. Example 7 is a very thick, hazy/cloudy gel that does not flow readily and its properties are similar to those of the bulk silicone elastomer. It applies smoothly to skin leaving a matte, extremely smooth low friction film. Example 8 shows signs of separation and has a small clear light amber colored layer on the bottom after 3 months storage at room temperature. It is a viscous opaque liquid that applies smoothly on skin leaving a durable, somewhat oily, water resistant shiny film. Example 9 is a light amber colored, hazy, viscous liquid with some white silicone elastomer particles floating in it. The properties are those of Polyderm PPI PGR providing good shine, but the films have a heavy feeling "drag" and sticky feel. Example 8, the 50/50 blend, again shows the most utility, finding applications in lip stick and lip gloss formulas where shine and durable film formation without stickiness are desirable properties. This combination has significantly less tack than the Polyderm PPI PGR and forms a film that has about the same shine as Polyderm PPI PGR.

| Ingredients | Example 10 % w/w | Example 11 % w/w | Example 12 % w/w |
|---|---|---|---|
| Silicone Elastomer (D5-6) | 99.0 | 50.0 | 1.0 |
| Polyderm PPI SA | 1.0 | 50.0 | 99.0 |
| | 100.0 | 100.00 | 100.00 |

These examples are mixtures made from Polyderm PPI SA which is a polyurethane made from isophorone diisocyanate and the two mole ethoxylate of soyamine and the same silicone elastomer D5-6 that was used in the previous examples. Polyderm PPI SA is used as a conditioning, emollient and deposition increasing agent in cosmetics and hair care products. This polymer has high deposition, presumably because it is cationic and very high tack. Example 10 is a very thick, hazy/cloudy gel that does not flow easily and its properties are similar to those of the bulk silicone elastomer. It applies smoothly to skin leaving a slightly shiny, extremely smooth low friction film. The film whitens and forms an emulsion (presumably a water-in-oil (w/o) type) and washes off easily with soap and water. Example 11 is a viscous opaque grainy looking paste that spreads smoothly on skin making an oily, but not sticky feeling film. The film whitens when water is applied (again presumably forming an emulsion) and washes off easily. It readily forms an emulsion when mixed with water (2 parts Example 11 to 1 part water). Emulsification is increased by adding acid and protonating the amine. Example 12 is a light amber colored, hazy, viscous liquid with some white silicone elastomer particles floating in it. The properties are those of Polyderm PPI SA providing good shine, but the films have a heavy feeling, a lot of "drag" and a sticky feel. Examples 10 and 11, are emulsifiable making them easier to incorporate in emulsion and water containing formulas. Example 11 also has good shine and forms a smooth, non tacky, oily film on skin.

| Ingredients | Example 13 w/w | Example 14 % w/w | Example 15 % w/w |
|---|---|---|---|
| Silicone Elastomer (D5-6) | 99.0 | 50.0 | 1.0 |
| Polyderm PPI SI-WI | 1.0 | 50.0 | 99.0 |
| | 100.0 | 100.00 | 100.00 |

These examples are mixtures made from Polyderm PPI SI-WI which is a polyurethane made from isophorone diisocyanate and a bis-propoxylated polydimethylsiloxane and the same silicone elastomer D5-6 that was used in the previous examples. Polyderm PPI SI-WI is used as a conditioning, emollient and friction reducing agent in cosmetics and hair care products. This polymer has high deposition, good shine and relatively low tack. Example 13 is a very thick, hazy/cloudy gel that does not flow easily and its properties are similar to those of the bulk silicone elastomer. It applies smoothly to skin leaving a slightly shiny, extremely smooth low friction film. Example 14 is a free flowing, low viscosity opaque liquid that separates into two layers upon standing. It spreads smoothly on skin making an oily, but not sticky feeling, very shiny film. Example 15 is a light amber colored, hazy, viscous liquid with some white silicone elastomer particles floating in it. The properties are those of Polyderm PPI SI-WI providing good shine, but with some "drag" and an oily feel. Example 14 is an especially useful combination that finds use in hair care conditioners by improving wet combing and shine.

| Ingredients | Example 16 % w/w | Example 17 % w/w | Example 18 % w/w |
|---|---|---|---|
| Silicone Elastomer (IDD-6) | 99.0 | 50.0 | 1.0 |
| Polyderm PPI SA | 1.0 | 50.0 | 99.0 |
| | 100.0 | 100.00 | 100.00 |

These examples are mixtures made from Polyderm PPI SA which is the same polyurethane material used in examples 10, 11 and 12. The silicone elastomer IDD-6 is a Silicone Elastomer made per U.S. Pat. No. 6,936,686, from a polyorganohydrosiloxane of about 3500 to 4000 molecular weight and with 6 to 7 hydrosilane groups per molecule reacted with a 20,000 to 25,000 molecular weight vinyl terminated polydimethylsiloxane in a reaction medium of isododecane (IDD) at ~12% w/w concentration. After polymerization, the elastomer concentration is reduced to 6% w/w by the addition of isododecane. Example 16 is a very thick, crystal clear, "rubbery" gel that does not flow easily and has noticeable "tack" and adhesion to skin. It applies smoothly to skin leaving a matte, extremely smooth low friction film. The film does not wash off easily, but it does "wet" when water is applied. Example 17 separates into two immiscible phases. One phase is a liquid that is similar to Polyderm PPI SA, and the other is a viscous opaque paste. The two components do not mix readily so that evaluation of the film and aesthetic properties of the mixture is difficult. Example 18 is an amber colored, hazy, viscous liquid. The applied film properties are essentially those of Polyderm PPI SA having good shine, but with a heavy feeling, a lot of "drag" and a sticky feel. The lack of shine and the wet ability of the Example 16 films makes this a good candidate for use in sunscreen and makeup products.

| Ingredients | Example 19 % w/w | Example 20 % w/w | Example 21 % w/w |
|---|---|---|---|
| Silicone Elastomer (IDD-6) | 99.0 | 50.0 | 1.0 |
| Polyderm PPI SA-15 | 1.0 | 50.0 | 99.0 |
| | 100.0 | 100.00 | 100.00 |

These examples are mixtures made from Polyderm PPI SA-15, a polyurethane made from isophorone diisocyanate and a fifteen mole ethoxylate of soyamine. The Polyderm SA-15 is clearly water soluble in all dilutions producing lubricious solutions that are used as conditioners in hair care products. The silicone elastomer IDD-6 is the same one that was used in the previous examples containing isododecane and 6% silicone elastomer solids. Example 19 is a very thick, hazy/cloudy gel that does not flow easily and its properties are similar to those of Example 16. It applies smoothly to skin leaving a slightly shiny, smooth film that "wets" when water is applied (it does not repel water as the silicone elastomer IDD-6 product alone does). Example 20 separates into two phases that do not mix well. One phase is an amber liquid that behaves like Polyderm SA-15 and the other phase is similar to Example 19. Example 21 is an amber colored, hazy, viscous liquid. The applied film properties are essentially those of Polyderm PPI SA-15 in that it has good shine, but with a heavy feeling, a slight "drag" and a somewhat sticky feel. It washes off easily with water leaving no residue. Example 19 is an interesting combination that finds use in sunscreen and makeup products.

| Ingredients | Example 22 % w/w | Example 23 % w/w | Example 24 % w/w |
|---|---|---|---|
| Silicone Elastomer (IDD-6) | 99.0 | 50.0 | 1.0 |
| Monoderm I-16 | 1.0 | 50.0 | 99.0 |
| | 100.0 | 100.00 | 100.00 |

These examples are mixtures made from Monoderm I-16 which is described in U.S. Pat. No. 6,583,106, which is incorporated by reference herein. It is a diurethane made from isophorone diisocyanate and isocetyl alcohol (2-hexyldecanol). The Monoderm I-16 is a water white viscous liquid that is soluble in lower alcohols, esters and hydrocarbons and is water insoluble. It forms a lubricious, very shiny, non-tacky film on skin the resists wash off with water and surfactants. The silicone elastomer IDD-6 is the same one that was used in the previous examples. Example 22 is a very thick, clear gel that is similar in appearance and performance to the original Silicone Elastomer Gel. It applies smoothly to skin leaving a matte, smooth film that does not wet with water. Example 23 is an opaque free flowing liquid that leaves a shiny, water wash-off resistant non-greasy feeling film on skin. There appears to be some separation of the elastomer as a soft gel on the surface of the liquid, but it easily mixes into the liquid when stirred. Example 24 is a clear, water white, viscous liquid similar in appearance and properties to Monoderm I-16 with the exception that there are many small white flocculent particles (probably elastomer) distributed throughout the liquid. Example 23 is the most interesting member of these examples and finds uses in make-up products and possibly fragrance applications.

| | Dimethicone/Soyamine/IPDI Copolymers | |
|---|---|---|
| Ingredients | Example 25 % w/w* | Example 26 % w/w* |
| A) Bis-PEG-1-Dimethicone | 94.477 | 93.117 |
| B) PEG-2 Soyamine | 0.720 | 2.150 |
| C) Isophorone Diisocyanate | 4.800 | 4.730 |
| D) Tin Octanoate | 0.003 | 0.003 |
| | 100.000 | 100.000 |

*The reactions were run based upon the reactants molecular weights using the desired molar ratios to calculate the reactant amount - transcribing these amounts to percentages causes decimal point errors that are the result of rounding.

Examples 25 and 26 are polyurethane copolymers that combine a silicone (polydimethylsiloxane) functionality with a soyamine moiety. The purpose is to produce a polymer that has compatibility with silicones that can be crosslinked (through the double bond of the soy fatty acid residue) with a dimethylsiliconhydride containing dimethicone polymer. In both Examples, ingredients A) and B) are loaded into a suitable vessel equipped with heating, mixing, nitrogen sparging and vacuum. They are mixed and heated (120° C.) under vacuum to dry. The batch is cooled to 95° C., stirring is continued, vacuum is stopped and ingredient D) is added. Nitrogen is begun and ingredient C) is slowly added (dropwise). Once addition is complete, nitrogen is stopped, vacuum is begun and the batch is stirred at 90-95° C. for 2 to 3 hours and until there is no detectable —NCO peak in the IR spectrum. These copolymers are used without further refinement in the subsequent examples.

| Silicone/Polyurethane Elastomers* | | |
|---|---|---|
| Ingredients | Example 27 % w/w | Example 28 % w/w |
| Isododecane | 84.550 | 84.550 |
| Vinyl terminated polydimethylsiloxane | 9.400 | 9.400 |
| polydimethylsiloxane with 6 to 7 pendant dimethyl hydrosilane groups | 1.000 | 1.000 |
| C-12 alpha-olefin | 0.010 | 0.010 |
| Example 25 | 5.000 | — |
| Example 26 | — | 5.000 |
| Platinum Catalyst | 0.040 | 0.040 |
| | 100.000 | 100.000 |

*These examples are prepared using the crosslinking and reaction technology described in U.S. Pat. No. 6,583,106, which is incorporated by reference.

Both Examples are clear smooth, elastic, sticky gels as prepared at 15.5% solids. Both Examples were further reduced to 6% solids concentration using isododecane as the solvent by first dispersing the gel, as made, in the solvent using a Cowles disperser blade and stirring for 30 min. followed by mixing with a Sliverson homogenizer @ 3500 rpm for 5 min. to produce a smooth, clear, slowly flowing, water white gel. Other solvents that may be used are: cyclomethicone, low viscosity dimethicones, cosmetic esters, low molecular weight alcohols and other hydrocarbon solvents.

Emulsions were then made using both of the Examples 27 and 28-6% solids gels as follows:

| Ingredients | Example 29 gms | Example 30 gms |
|---|---|---|
| Example 27 (6% solids Gel in isododecane) | 12.0 | — |
| Example 28 (6% solids Gel in isododecane) | — | 12.0 |
| 50% Citric Acid aq. Solution | 0.5 | 0.5 |
| Reverse Osmosis Water | 36.0 | 48.0 |
| | 100.0 | 100.0 |

Example 29 is a water-in-oil (w/o) emulsion with a 75% internal phase made by simple hand stirring of the water into the silicone/polyurethane copolymer gel. For use in personal care products additives such as: antimicrobial preservatives, colorants, pigments, antioxidants, chelating agents, salts, fragrances, botanical extracts, proteins, emulsion stabilizers, emulsifiers, viscosity builders and active ingredients such as: sunscreens, antiperspirants, antidandruff agents, skin tanning agents and skin whitening agents. Similar ingredients would be added if this types of w/o emulsion was to be used for pharmaceutical applications, except that additionally, the pharmaceutical active material would be added. It is further envisioned that additional emollient ingredients such as—for example, but not limited to: vegetable oils, animal fats, mineral oils, petrolatums, cosmetic waxes, cosmetic esters, polydimethyl siloxanes, polyphenylmethyl siloxanes, cyclomethicones, polyurethanes, polyacrylates, polyethylenes, polybutenes and polydecenes. Additionally, Example 29 and its dilutions may be used as additive ingredients to stabilize emulsions formed by other polymeric emulsifiers and or conventional emulsifier systems.

Example 30 is a water-in-oil (w/o) emulsion with an 80% internal phase made by simple hand stirring of the water into the silicone/polyurethane copolymer gel. For use in personal care products additives such as: antimicrobial preservatives, colorants, pigments, antioxidants, chelating agents, salts, fragrances, botanical extracts, proteins, emulsion stabilizers, emulsifiers, viscosity builders and active ingredients such as: sunscreens, antiperspirants, antidandruff agents, skin tanning agents and skin whitening agents. Similar ingredients would be added if this types of w/o emulsion was to be used for pharmaceutical applications, except that additionally, the pharmaceutical active material would be added. It is further envisioned that additional emollient ingredients such as—for example, but not limited to: vegetable oils, animal fats, mineral oils, petrolatums, cosmetic waxes, cosmetic esters, polydimethyl siloxanes, polyphenylmethyl siloxanes, cyclomethicones, polyurethanes, polyacrylates, polyethylenes, polybutenes and polydecenes. Additionally, Example 29 and its dilutions may be used as additive ingredients to stabilize emulsions formed by other polymeric emulsifiers and or conventional emulsifier systems.

What we claim is:

1. A composition comprising an admixture of a silicone elastomer and a polyurethane compound wherein said silicone elastomer comprises about 0.5% to about 99.5% by weight of said admixture and said polyurethane compound comprises about 0.5% to about 99.5% by weight of said admixture, wherein said polyurethane is a compound of formula 4:

Formula 4 where n is 5 to 100, and
$R_{10}$ is a —$CH_2$—CH—(CH—($CH_2$)$_7$ radical.

2. A composition comprising an admixture of a silicone elastomer and a polyurethane compound wherein said silicone elastomer comprises about 0.5% to about 99.5% by weight of said admixture and said polyurethane compound comprises about 0.5% to about 99.5% by weight of said admixture, wherein said polyurethane is a compound of formula 5:

Formula 5 where n is 5 to 100, and
$R_{10}$ is a —$CH_2$—CH=CH—($CH_2$)$_7$ radical.

3. A personal care composition comprising a composition according to claim 1 in combination with at least two components selected from the group consisting of water, an aqueous solvent, a non-aqueous solvent, emollients, humectants, oils, conditioning agents, surfactants, thickeners/thickening agents, stiffening agents, emulsifiers, medicaments, fragrances, preservatives, deodorant components, anti-perspirant compounds, skin protecting agents, pigments, dyes, coloring agents, sunscreens and mixtures thereof.

4. A personal care composition comprising a composition according to claim 2 in combination with at least two components selected from the group consisting of water, an aqueous solvent, a non-aqueous solvent, emollients, humectants, oils, conditioning agents, surfactants, thickeners/thickening agents, stiffening agents, emulsifiers, medicaments, fragrances, preservatives, deodorant components, anti-perspirant compounds, skin protecting agents, pigments, dyes, coloring agents, sunscreens and mixtures thereof.

* * * * *